United States Patent
Smits et al.

(10) Patent No.: US 9,763,799 B2
(45) Date of Patent: *Sep. 19, 2017

(54) REVERSE SHOULDER PROSTHETIC

(71) Applicant: Biomet Manufacturing, LLC, Warsaw, IN (US)

(72) Inventors: Aaron Smits, Fort Wayne, IN (US); Kurt Schmidt, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/062,325

(22) Filed: Mar. 7, 2016

(65) Prior Publication Data

US 2016/0256289 A1 Sep. 8, 2016

Related U.S. Application Data

(63) Continuation of application No. 13/803,142, filed on Mar. 14, 2013, now Pat. No. 9,278,005, which is a
(Continued)

(51) Int. Cl.
*A61F 2/40* (2006.01)
*A61F 2/30* (2006.01)

(52) U.S. Cl.
CPC ........... *A61F 2/4081* (2013.01); *A61F 2/40* (2013.01); *A61F 2/4014* (2013.01); *A61F 2002/3069* (2013.01); *A61F 2002/30331* (2013.01); *A61F 2002/30332* (2013.01); *A61F 2002/30367* (2013.01); *A61F 2002/30382* (2013.01); *A61F 2002/30431* (2013.01); *A61F 2002/30433* (2013.01); *A61F 2002/30507* (2013.01); *A61F 2002/4022* (2013.01); *A61F 2002/4085* (2013.01)

(58) Field of Classification Search
CPC ................................ A61F 2/40; A61F 2/4081
See application file for complete search history.

(56) References Cited

U.S. PATENT DOCUMENTS

| 6,660,039 B1 | 12/2003 | Evans et al. |
| 8,454,702 B2 | 6/2013 | Smits et al. |
| (Continued) | | |

FOREIGN PATENT DOCUMENTS

| EP | 1656910 A1 | 5/2006 |
| EP | 1782764 A2 | 5/2007 |
| (Continued) | | |

OTHER PUBLICATIONS

"U.S. Appl. No. 13/009,896, Non Final Office Action mailed Aug. 1, 2012", 9 pgs.
(Continued)

*Primary Examiner* — Brian Dukert
(74) *Attorney, Agent, or Firm* — Schwegman Lundberg & Woessner, P.A.

(57) ABSTRACT

A reverse modular humeral implant for implantation into a humerus that includes a natural humeral shaft and a natural humeral head. The implant includes a humeral stem implantable into the natural humeral shaft, and an adapter couplable to the humeral stem, the adapter including an anchoring projection configured to be coupled to a convex bearing.

13 Claims, 7 Drawing Sheets

Related U.S. Application Data continuation of application No. 13/009,896, filed on Jan. 20, 2011, now Pat. No. 8,454,702.

(56) References Cited

U.S. PATENT DOCUMENTS

| | | | |
|---|---|---|---|
| 9,278,005 | B2 | 3/2016 | Smits et al. |
| 2004/0220673 | A1 | 11/2004 | Pria |
| 2006/0200248 | A1 | 9/2006 | Beguin et al. |
| 2009/0192621 | A1 | 7/2009 | Winslow et al. |
| 2010/0274359 | A1* | 10/2010 | Brunnarius ......... A61F 2/30734 623/19.13 |
| 2013/0197650 | A1 | 8/2013 | Smits et al. |

FOREIGN PATENT DOCUMENTS

| | | |
|---|---|---|
| EP | 1787603 A1 | 5/2007 |
| EP | 2665445 A1 | 11/2013 |
| EP | 2665445 B1 | 8/2016 |
| WO | WO2012099779 A1 | 7/2012 |

OTHER PUBLICATIONS

"U.S. Appl. No. 13/009,896, Notice of Allowance mailed Feb. 1, 2013", 8 pgs.

"U.S. Appl. No. 13/009,896, Prelimianry Amendment filed May 25, 2012", 15 pgs.

"U.S. Appl. No. 13/009,896, Response filed Oct. 19, 2012 to Non Final Office Action mailed Aug. 1, 2012", 15 pgs.

"U.S. Appl. No. 13/803,142, Examiner Interview Summary mailed Oct. 8, 2015", 3 pgs.

"U.S. Appl. No. 13/803,142, Non Final Office Action mailed Jul. 13, 2015", 8 pgs.

"U.S. Appl. No. 13/803,142, Notice of Allowance mailed Nov. 3, 2015", 5 pgs.

"U.S. Appl. No. 13/803,142, Prelimianry Amendment filed May 23, 2013", 9 pgs.

"U.S. Appl. No. 13/803,142, Response filed Oct. 12, 2015 to Non Final Office Action mailed Jul. 13, 2015", 9 pgs.

"European Application Serial No. 12701310.0, Examination Notification Art. 94(3) mailed Jul. 7, 2015", 4 pgs.

"European Application Serial No. 12701310.0, Office Action mailed Sep. 13, 2013", 2 pgs.

"International Application Serial No. PCT/US2012/021176, International Preliminary Report on Patentability mailed Aug. 1, 2013", 7 pgs.

"International Application Serial No. PCT/US2012/021176, International Search Report mailed Mar. 19, 2012", 4 pgs.

"International Application Serial No. PCT/US2012/021176, Written Opinion mailed Mar. 19, 2012", 5 pgs.

\* cited by examiner

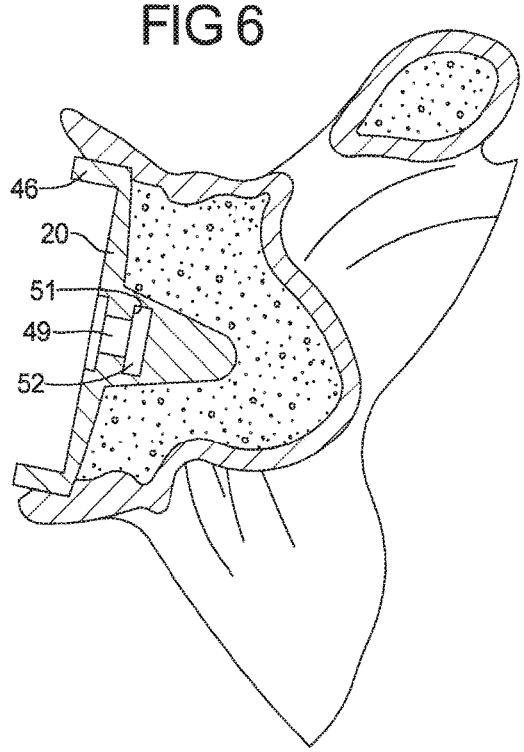
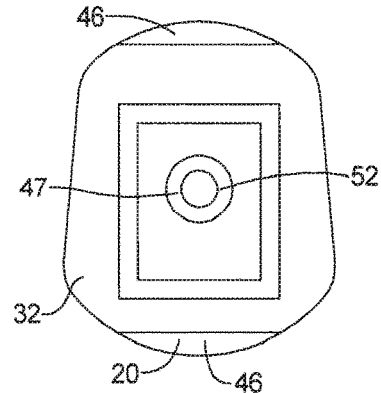
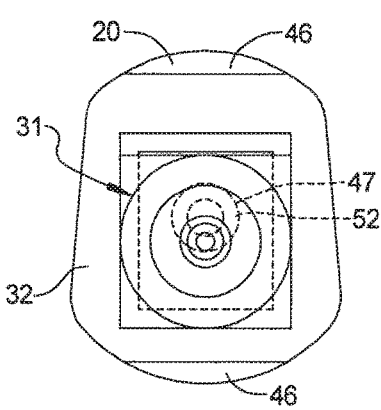
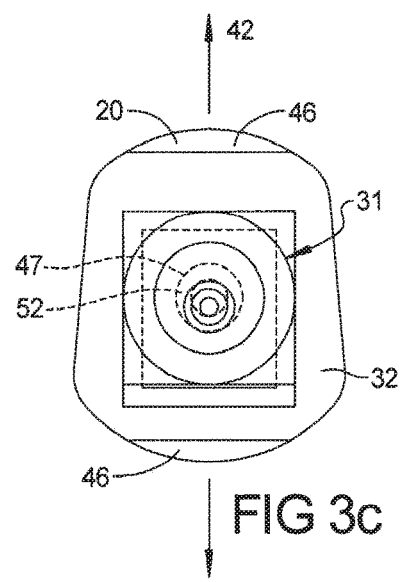

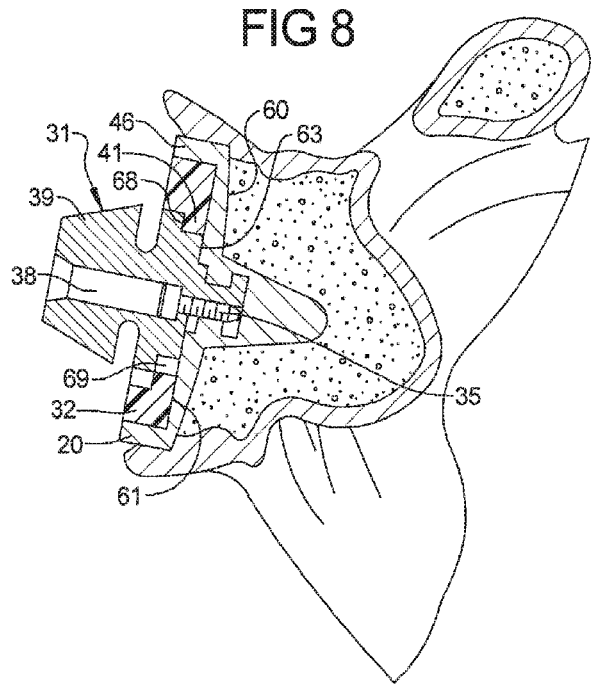
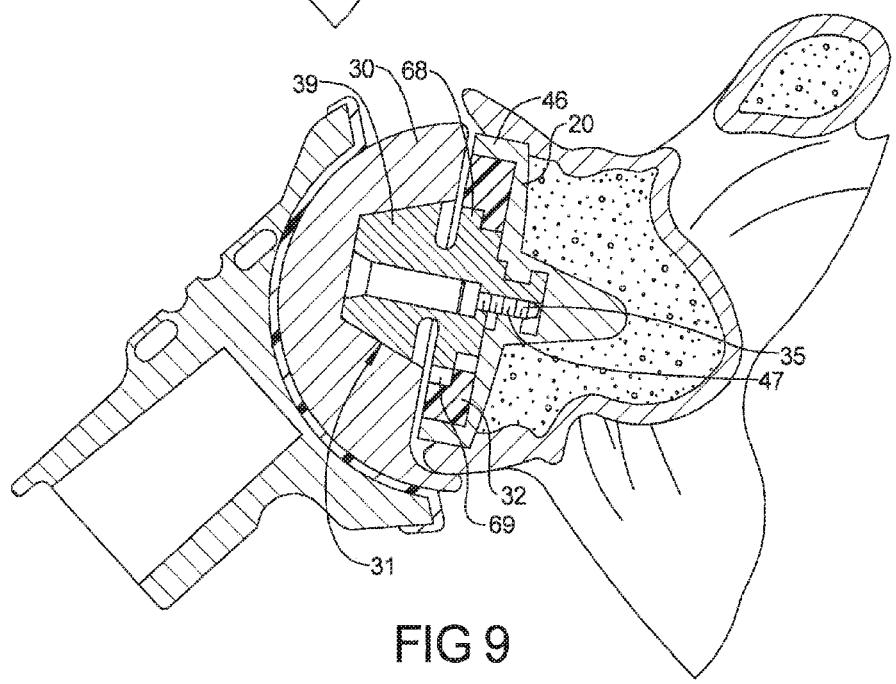

REVERSE SHOULDER PROSTHETIC

CROSS-REFERENCE TO RELATED APPLICATIONS

This application is a continuation of U.S. patent application Ser. No. 13/009,896 filed on Jan. 20, 2011. The entire disclosure of the above application is incorporated herein by reference.

FIELD

The present disclosure relates to a humeral prosthesis for total shoulder joint replacement and generally includes a prosthetic humeral stem, a bearing coupling mechanism, and a prosthetic head which replaces a portion of the humeral joint.

BACKGROUND

This section provides background information related to the present disclosure which is not necessarily prior art.

It is not uncommon for the exterior surface of the humeral head to be damaged or defective. Conventionally, a variety of humeral head resurfacing implants exist for repairing humeral head surfaces. While conventional humeral head resurfacing implants are suitable for their intended uses, such implants are subject to improvement.

Conventional humeral implants fail to accommodate patients having inadequate skeletal structure needed during a revision procedure.

Specifically, conventional implants do not permit articulation between the implant and the concave undersurface of the coracoacromial arch of the scapula, the coracoacromial arch being a structural component of the shoulder comprising the coracoacromial ligament, coracoid process, and acromion. Thus, there is a need for a humeral implant that permits revision of the articulation surface to allow proper articulation dynamics.

SUMMARY

This section provides a general summary of the disclosure, and is not a comprehensive disclosure of its full scope or all of its features. Various aspects of the teachings provide a modular humeral implant and associated kit and method for implantation into a humerus that includes a natural humeral shaft and a natural humeral head.

A modular reverse shoulder prosthetic for a revision procedure is taught. The reverse shoulder prosthetic can have a glenoid tray configured to be implanted into a resected glenoid. The tray can have an opposed bearing mounting surface defining a coupling aperture therein. The aperture has a first portion with a first internal diameter and a second portion with a second internal diameter, the second internal diameter being larger than the first diameter, wherein the first portion can be disposed between the second portion and the bearing mounting surface and wherein a locking surface can be defined at an interface between the first and second portions. A bearing coupling member is provided which is configured to engage the bearing mounting surface, the bearing coupling member can have a coupling flange extending generally perpendicular therefrom. The flange can have a depending locking member configured to be disposed through the first portion and into the second portion of the coupling aperture and to engage the locking surface. The mounting portion having a bearing coupling side can have a coupling taper configured to mate to a corresponding taper on a bearing member.

According to alternate teachings, the shoulder prosthetic can have a glenoid tray configured to be implanted into the resected glenoid. The tray can have a glenoid interface surface with a depending coupling stem and an opposed bearing mounting surface. The bearing mounting surface defines a coupling aperture therein. The coupling aperture can have a first portion with a first internal diameter and a second portion with a second internal diameter. The second internal diameter can be larger than the first diameter, and the first portion can be disposed between the second portion and the bearing mounting surface. A locking surface can be defined at the interface between the first and second portions. The bushing member is first disposed within the glenoid tray, and defines an aperture having a plurality of generally planar bearing surfaces defining a bushing member bearing ledge. A bearing coupling member is disposed within the bushing member.

The bushing member can have a planar interface surface configured to engage the bearing mounting surface. The bearing mounting surface can have a coupling flange extending generally perpendicular therefrom. A bearing coupling member can be disposed therein. The bearing coupling member can have a bearing coupling side having a coupling surface configured to mate to a corresponding surface on a bearing member.

According to alternate teachings, the bearing coupling member can define a bearing coupling member coupling ledge configured to slidably engage the bushing member bearing ledge when the bearing coupling member is engaged with the bushing and the glenoid tray. The bearing coupling member is translatable with respect to the bushing.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The drawings described herein are for illustrative purposes only of selected embodiments and not all possible implementations, and are not intended to limit the scope of the present disclosure.

FIGS. 3a-3c are end views of the coupling member, bushing, and tray according to the present teachings;

FIGS. 6-9 represent cross-sectional views of a revision procedure.

DETAILED DESCRIPTION

Example embodiments will now be described more fully with reference to the accompanying drawings.

Figure 1:
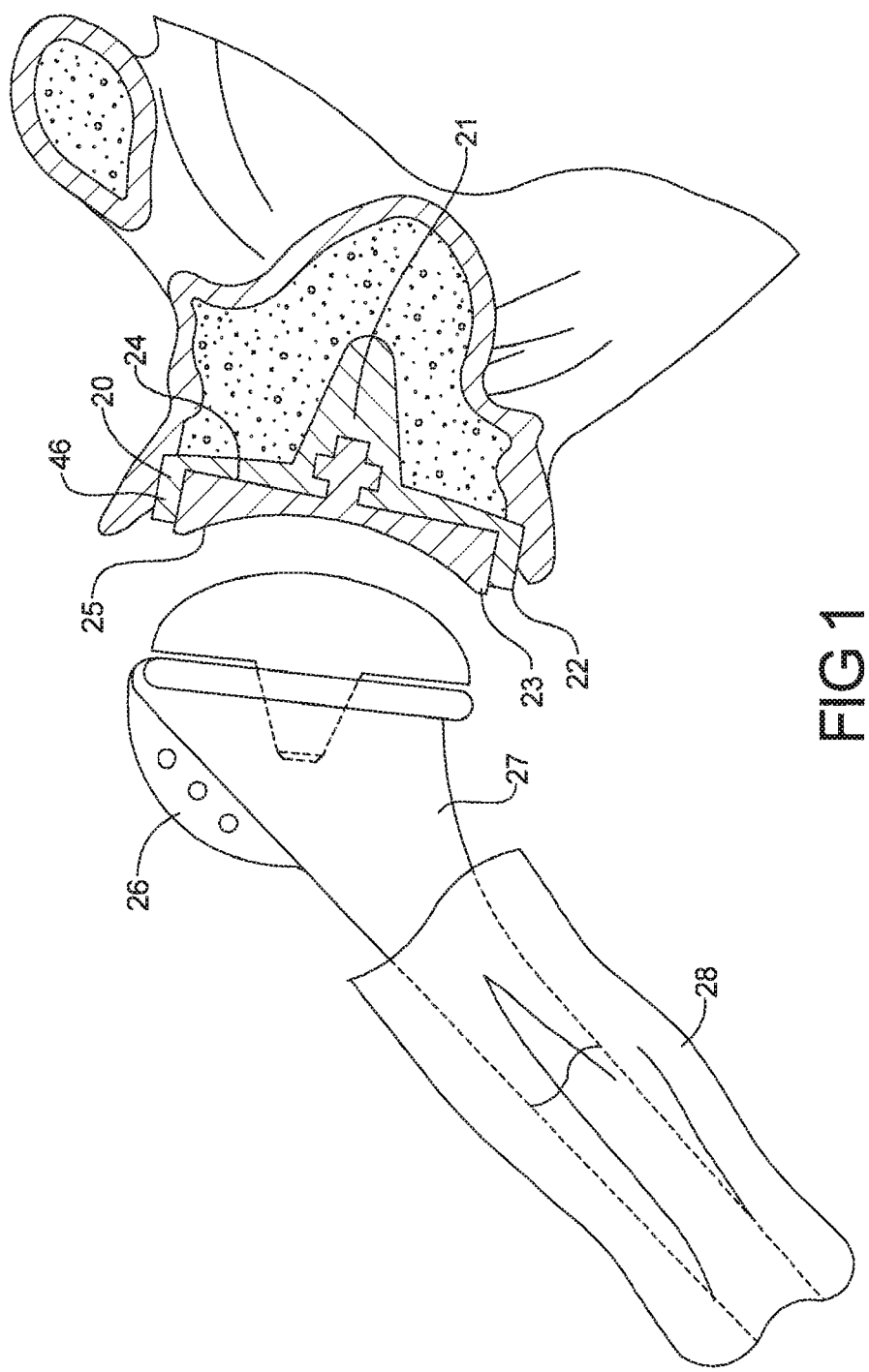
FIG. 1 is a view of a humeral implant according to the prior art.

FIG. 1 represents a shoulder prosthetic system according to the prior art. Shown is a coupling, bearing or glenoid tray 20 having a dependent stem 21 and fixation edge 22. Disposed within the glenoid tray 20 is a polymer glenoid 23 having a mounting interface 24 and concave bearing surface 25. The concave bearing surface 25 is configured to interface with the articulating surface of a humeral prosthetic 26. Generally, the concave bearing surface 25 is configured to interface with a humeral prosthetic.

Figure 2:
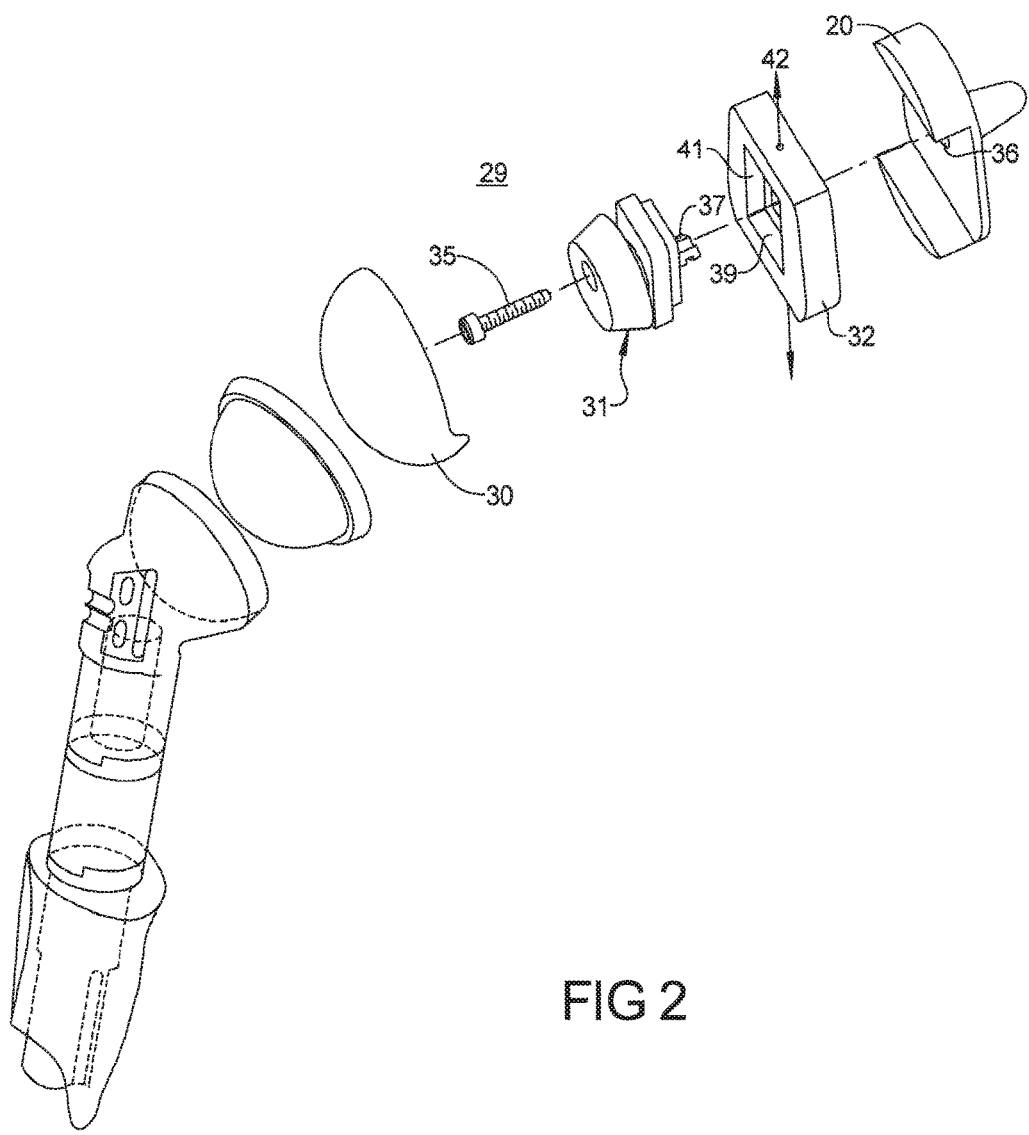
FIG. 2 is an exploded view of a reverse humeral implant according to the present teachings.

The humeral prosthetic has a stem 27 which can be coupled to the medullary canal of a resected humerus 28. Alternatively, a short stem head prosthetic can be used. As further described below, the prosthetic system can at least be partially removed in a revision procedure. FIG. 2 represents an exploded perspective view of the reverse shoulder system 29 according to the present teachings. The reverse shoulder system 29 utilizes the glenoid tray 20 to couple a reverse shoulder head member 30 to the prepared glenoid after a traditional glenoid member has been removed in a revision procedure.

As described below, the head member 30 is coupled to the glenoid tray 20 using an intermediary or bearing coupling member 31. Disposed about the bearing coupling member 31 is a polymer sleeve, bushing member or bushing 32, which can be coupled to the bearing coupling member 31 and the glenoid tray 20. The bearing coupling member 31 is non-rotatably fastened to the glenoid tray 20 using a fastener 35. In this regard, the bearing coupling member 31 has a generally cylindrical coupling flange 37 which is inserted into a bore 36 defined within the glenoid tray 20. The bushing 32 engages the fixation edge 22 to prevent rotation of the bearing coupling member 31.

The fastener 35 can be used to fixably couple the bearing coupling member 31 to the glenoid tray 20. The polymer bushing 32 defines an interior coupling bore 40 defining at least one flat bearing surface 39. Optionally, the interior coupling bore 40 can define four intercepting flat bearing surfaces which form a square or a rectangle. The interior coupling bore 40 radially supports the bearing coupling member 31 on a pair of parallel sides. As described below, the bearing coupling member 31 is slid along the axis 42 of the interior coupling bore 40 to move the locking member or coupling flange 37 from an unengaged to an engaged position.

FIGS. 3a-3c represent end views of the glenoid tray 20 and associated bushing 32. Shown are snapped ends 46 which rotationally lock both the glenoid bearing or bushing into the glenoid tray 20. As best seen in FIGS. 3a and 4, the glenoid tray 20 defines a central coupling bore 47. The coupling bore 47 has a first portion 49 having a first diameter, and a second portion 50 having a second diameter. The second portion 50 defines a locking surface 51 configured to interface with a coupling flange of the bearing coupling member 31.

Figure 4A:
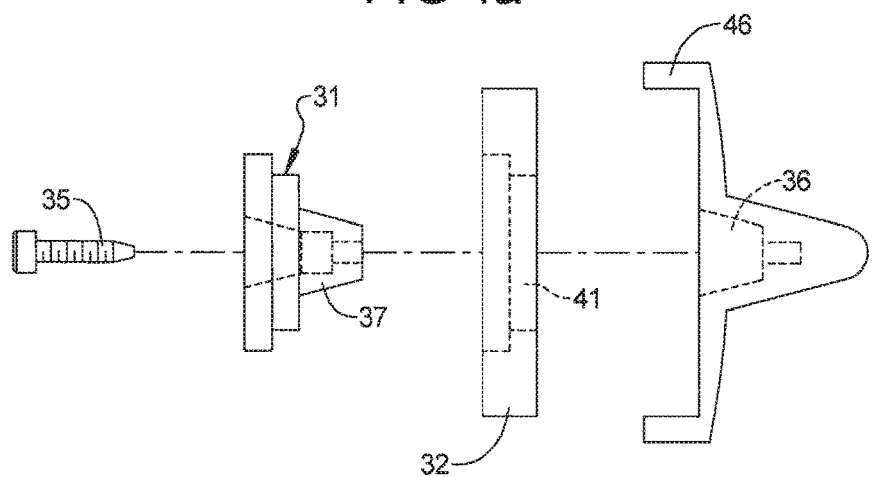
FIGS. 4a-4d are side exploded views of a humeral implant subassembly using the coupling mechanism, bushing, and tray according to the present teachings.
Figure 4B:
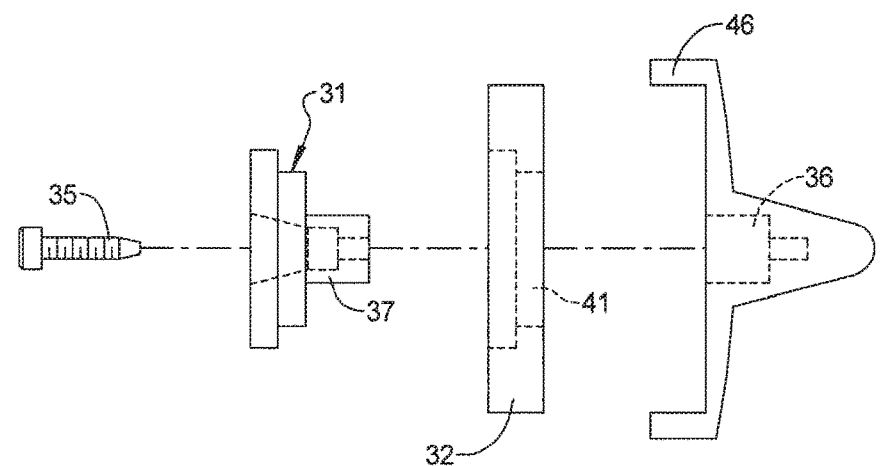

FIGS. 4a-4d represent exploded views of alternate mechanisms for coupling the bearing coupling member 31 to the glenoid tray 20. While similar, each coupling mechanism has different advantages. As shown in FIGS. 4a and 4b, the bearing coupling member 31 can be coupled through the interior coupling bore 40 defined in the bushing 32. The coupling flange 37 can take the form of a cylinder or coupling taper. Additionally, the-fastener 35 can be used to couple the bearing coupling member 31 to the glenoid tray 20.

Figure 4C:
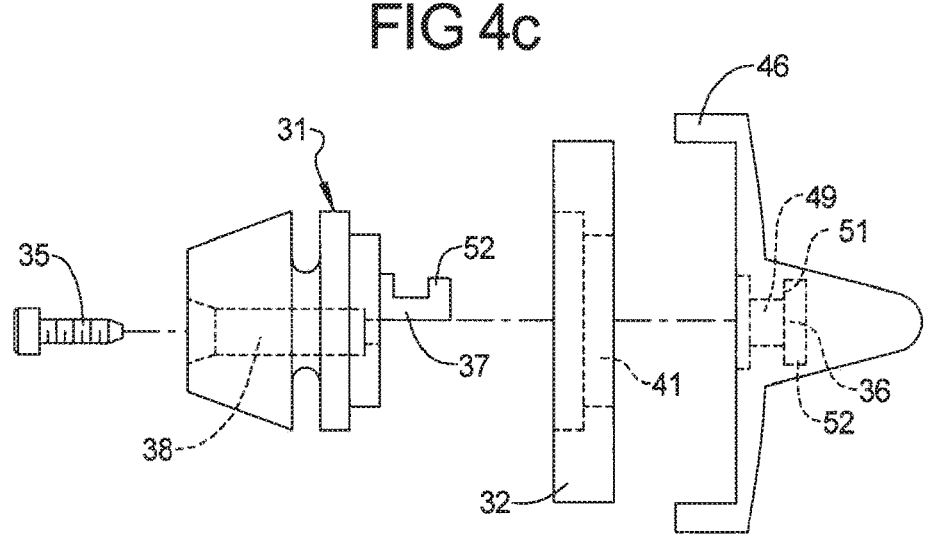
Figure 4D:
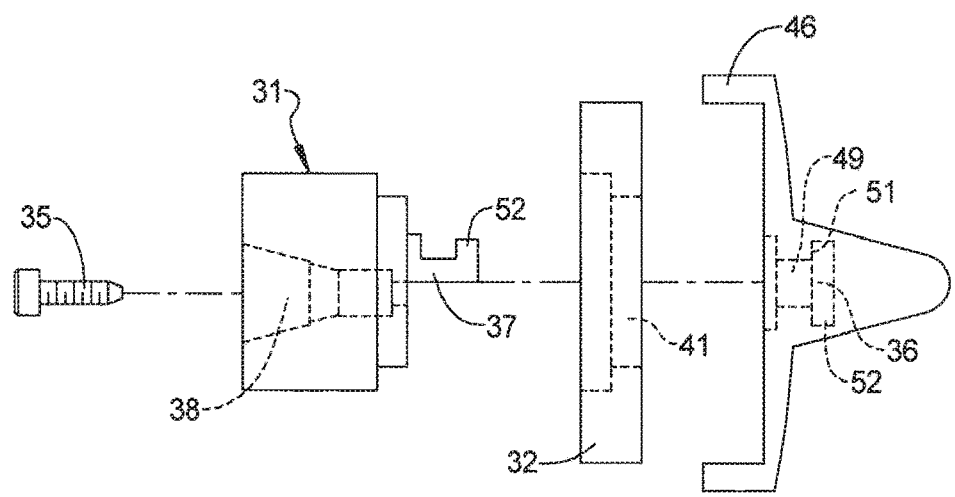

As shown in FIGS. 4c and 4d, the bearing coupling member 31 can be coupled through the interior coupling bore 40 defined in the bushing 32 and into the first and second portion of the bore 36. The coupling flange 37 takes the form of a cylinder coupling flange. The coupling flange 37 has a depending flange 53 configured to interface with the locking surface 51. The coupling flange 37 is centered at a location generally offset on a first side from the centerline of the bearing coupling member 31. The bearing coupling member 31 defines a throughbore 38 generally offset on a second opposed side from the centerline of the bearing coupling member 31. The fastener 35 can be passed through the throughbore 38 and at least partially into the first portion of the coupling bore to couple the bearing coupling member 31 to the glenoid tray 20.

Figure 5:
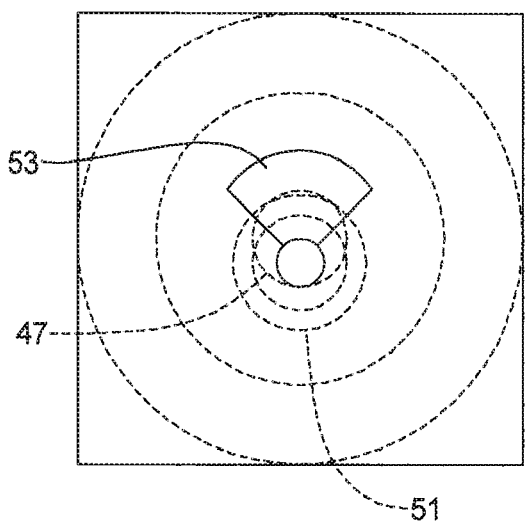
FIG. 5 is an assembled end view of the coupling mechanism and tray according to the present teachings in an engaged position.

As best seen in FIG. 5, the coupling mechanism depending flange 53 is configured to interface with the locking surface 51. The flange 53 is configured to fit through the smaller diameter first portion 49 of the coupling bore 47. It, therefore, has a cross-sectional area and geometry which allows its transfer from a first non-engaged position to an engaged position after the depending flange is passed through into the second portion 50. This engagement releasably locks the bearing coupling member 31 to the glenoid tray 20. The addition of the fastener through the offset throughbore 38 locks the coupling member in place. It is envisioned the coupling member can have either male or female locking tapers or an exterior coupling taper 43 to couple the head member 30 to the glenoid tray 20.

Figure 7:
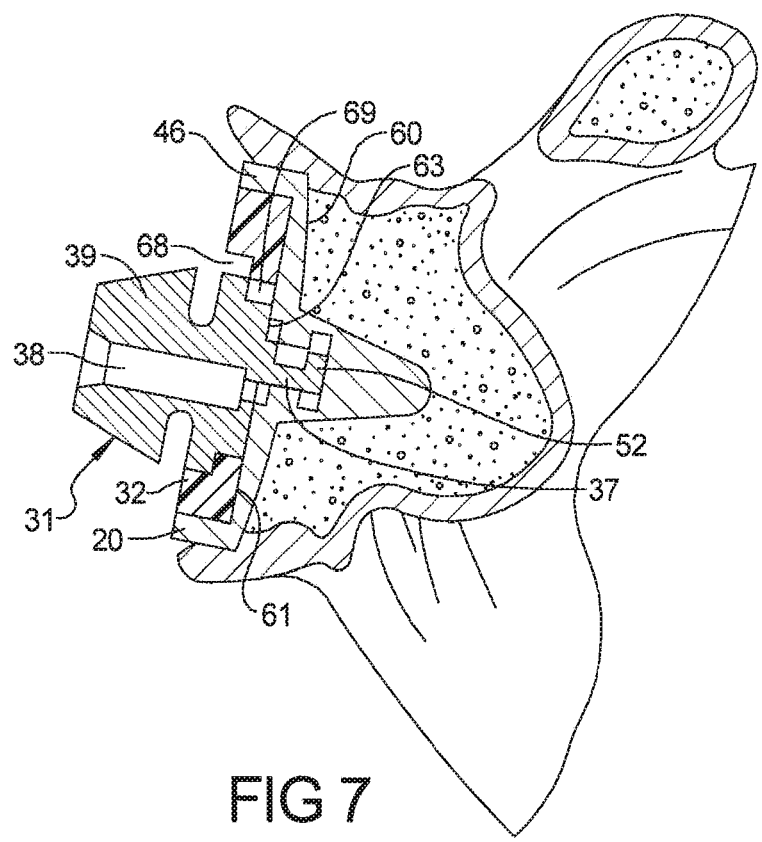

FIGS. 6-8 depict side exploded views of a procedure to couple the interface coupling system to the glenoid tray 20. In this regard, it is envisioned that the glenoid tray 20 could have been previously coupled to the glenoid in a traditional arthroplasty (see FIG. 1). FIG. 6 depicts the glenoid tray 20 coupled to a prepared glenoid. Shown is the central coupling bore 47 with associated first and second portions 49 and 50.

As shown in FIG. 7, after the bushing 32 is coupled to the glenoid tray 20, the bearing coupling member 31 is positioned though a bushing aperture or bore 41 in contact with a bearing surface of the glenoid tray 20. Defined about the external periphery of the bearing coupling member 31 can be a cutout or ledge portion configured to interface with a ledge defined within the bushing aperture or bore 41 of the spacer member.

The coupling flange 37 has an exterior surface having a generally fixed radius of curvature about the centerline defining the body. The coupling flange 37 generally can present a one-half cylinder which has a cross-sectional area smaller than the cross-sectional area of the coupling bore 47 in the glenoid tray 20. The flange extended ledge portion 52 extends generally perpendicular to a centerline defining the extending ledge portion 52. As shown in FIGS. 7 and 8, the ledge portion 52 is configured to interface with the locking surface 51.

The reverse shoulder prosthetic can have a glenoid tray 20 configured to be implanted into a resected glenoid. The glenoid tray 20 can have a glenoid interface surface 60 and an opposed bearing mounting surface 61. The bearing coupling member 31 can have a planar interface surface 63 configured to engage the bearing mounting surface 61.

Shown in FIG. 8, the bushing 32 defines bushing bore 41 having a plurality of generally planar bearing surfaces which define a bushing member bearing ledge 68. The bearing coupling member 31, disposed within the bushing 32, has a planar interface surface 69 configured to engage the bearing mounting surface 61. The bearing coupling member can be translated with respect to the glenoid tray 20. The bearing coupling member 31 can be translatable with respect to the glenoid tray 20 from an unlocked position to a locked position. The bearing coupling member 31 is translatable with respect to the glenoid tray in a direction parallel to the bearing mounting surface from a first unlocked position (FIG. 7) to a second locked position (FIG. 8).

As best seen in FIG. 9, a head 30 can be coupled to the exterior coupling taper 43 formed on the bearing coupling member 31. It is envisioned that the interfering ledges can hold the bushing 32 in place against the glenoid tray 20 and the bushing 32 inhibits rotation of the bearing coupling member 31.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections. these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method of implanting a shoulder prosthetic, the method corn prising:
   implanting a glenoid tray into a resected glenoid;
   engaging a bearing coupling member with a bearing mount surface of the glenoid tray;
   restricting relative rotation between the glenoid tray and the bearing coupling member with a bushing member disposed about the bearing coupling member;
   inserting a locking member into an interior coupling bore of the glenoid tray, the locking member being in a first position inside the interior coupling bore in which the beating coupling member is not locked to the glenoid tray, the locking member including a flange;
   moving the locking member in the interior coupling bore to a second position such that the flange engages a portion of the glenoid tray to lock the bearing coupling member to the glenoid tray;
   mating the bearing coupling member with a first bearing member having an articulation surface; and
   mating the first bearing member with a second beating member having an articulation surface, such that the first bearing member can articulate relative to the second bearing member by way of engagement of the articulation surfaces.

2. The method of claim 1, wherein moving the locking member to the second position comprises releasably locking the bearing coupling member to the glenoid tray.

3. The method of claim 1, wherein the interior coupling bore comprises a first part defining a first diameter and a second part defining a second diameter, and the second diameter is greater than the first diameter.

4. The method of claim 3, wherein the second position for the locking member is a position in which the locking member is disposed within the second part of the interior coupling bore.

5. The method of claim 4, further comprising translating the bearing coupling member relative to the bushing member to move the locking member to the second position.

6. The method of claim 1, wherein the first bearing member is a glenosphere having a spherical convex surface configured to interface with a concave bearing.

7. A method of implanting a shoulder prosthetic comprising:
   implanting a glenoid tray into a resected glenoid;
   non-rotatably engaging a bearing coupling member with a bearing mount surface of the glenoid tray;
   inserting a locking member into an interior coupling bore of the glenoid tray, the locking member being in a first position inside the interior coupling bore in which the bearing coupling member is not locked to the glenoid tray;
   translating the bearing coupling member perpendicular to a longitudinal axis of the interior coupling bore to a second position such that the bearing coupling member is locked to the glenoid tray;
   mating the bearing coupling member with a first bearing member having an articulation surface; and
   mating the first bearing member with a second bearing member having an articulation surface, such that the first bearing member can articulate relative to the second bearing member by way of engagement of the articulation surfaces.

8. The method of claim 7, further comprising positioning a bushing member about the bearing coupling member and non-rotatably engaging the bushing member with the glenoid tray.

9. The method of claim 7, wherein moving the locking member to the second position comprises releasably locking the bearing coupling member to the glenoid tray.

10. The method of claim 7, wherein the first bearing member is a glenosphere having a spherical convex surface configured to interface with a concave bearing.

11. A method of implanting a shoulder prosthetic comprising:
   implanting a glenoid tray into a resected glenoid;
   non-rotatably engaging a bearing coupling member with the glenoid tray;
   inserting a first portion of the bearing coupling member into an interior coupling bore of the glenoid tray, such that the bearing coupling member is unlocked relative to the glenoid tray, the first portion including a flange;
   translating the bearing coupling member perpendicular to a longitudinal axis of the glenoid tray to cause the flange to move to a locking position in which the flange lockingly engages with part of the interior coupling bore, such that the bearing coupling member is locked relative to the glenoid tray;
   mating the bearing coupling member with a first bearing member having an articulation surface; and
   mating the first bearing member with a second bearing member having an articulation surface, such that the first bearing member can articulate relative to the second bearing member by way of engagement of the articulation surfaces.

12. The method of claim 11, further comprising inserting the bearing coupling member into a bushing member and non-rotatably engaging the busing member to the glenoid tray.

13. The method of claim 11, wherein the first bearing member is a glenosphere having a spherical convex surface configured to interface with a concave bearing.

* * * * *

UNITED STATES PATENT AND TRADEMARK OFFICE
CERTIFICATE OF CORRECTION

PATENT NO. : 9,763,799 B2  
APPLICATION NO. : 15/062325  
DATED : September 19, 2017  
INVENTOR(S) : Smits et al.

Page 1 of 1

It is certified that error appears in the above-identified patent and that said Letters Patent is hereby corrected as shown below:

On the Title Page

On page 2, in Column 2, item (56) under "Other Publications", Line 1, delete "Prelimianry" and insert --Preliminary-- therefor On page 2, in Column 2, item (56) under "Other Publications", Line 11, delete "Prelimianry" and insert --Preliminary-- therefor In the Claims In Column 6, Line 28, in Claim 1, delete "corn prising:" and insert --comprising:-- therefor In Column 6, Line 38, in Claim 1, delete "beating" and insert --bearing-- therefor In Column 6, Line 46, in Claim 1, delete "beating" and insert --bearing-- therefor In Column 8, Line 25, in Claim 12, delete "busing" and insert --bushing-- therefor Signed and Sealed this  
Twenty-fourth Day of April, 2018

Andrei Iancu  
*Director of the United States Patent and Trademark Office*